US008354256B2

(12) United States Patent
Breneman et al.

(10) Patent No.: US 8,354,256 B2
(45) Date of Patent: Jan. 15, 2013

(54) **GLUCOAMYLASE AND *BUTTIAUXIELLA* PHYTASE DURING SACCHARIFICATION**

(75) Inventors: Suzanne Breneman, Orfordville, WI (US); Oreste J. Lantero, Jr., Trimble, MO (US); Bradley A. Paulson, Brodhead, WI (US); Jayarama K. Shetty, Pleasanton, CA (US)

(73) Assignee: Danisco US Inc., Palo Alto, CA (US)

( * ) Notice: Subject to any disclaimer, the term of this patent is extended or adjusted under 35 U.S.C. 154(b) by 683 days.

(21) Appl. No.: 12/400,732

(22) Filed: Mar. 9, 2009

(65) Prior Publication Data

US 2009/0246845 A1   Oct. 1, 2009

Related U.S. Application Data

(60) Provisional application No. 61/035,672, filed on Mar. 11, 2008.

(51) Int. Cl.
| | |
|---|---|
| C12P 7/02 | (2006.01) |
| C12P 7/08 | (2006.01) |
| C12Q 1/34 | (2006.01) |
| C12N 9/16 | (2006.01) |
| C12N 9/24 | (2006.01) |
| C12N 9/28 | (2006.01) |

(52) U.S. Cl. ........ 435/155; 435/196; 435/200; 435/202; 435/18

(58) Field of Classification Search .................. 435/155, 435/200, 201, 202, 203, 204, 196
See application file for complete search history.

(56) References Cited

U.S. PATENT DOCUMENTS

| | | | |
|---|---|---|---|
| 4,092,434 | A | 5/1978 | Yoshizumi et al. |
| 4,316,956 | A | 2/1982 | Lutzen |
| 4,514,496 | A | 4/1985 | Yoshizumi et al. |
| RE32,153 | E | 5/1986 | Tamura et al. |
| 4,587,215 | A | 5/1986 | Hirsh |
| 4,618,579 | A | 10/1986 | Dwiggins et al. |
| 4,760,025 | A | 7/1988 | Estell et al. |
| 5,000,000 | A | 3/1991 | Ingram et al. |
| 5,028,539 | A | 7/1991 | Ingram et al. |
| 5,424,202 | A | 6/1995 | Ingram et al. |
| 5,514,583 | A | 5/1996 | Picataggio et al. |
| 5,554,520 | A | 9/1996 | Fowler et al. |
| 5,612,055 | A | 3/1997 | Bedford et al. |
| 5,763,385 | A | 6/1998 | Bott et al. |
| 5,824,532 | A | 10/1998 | Barnett et al. |
| 5,958,739 | A | 9/1999 | Mitchinson et al. |
| 6,008,026 | A | 12/1999 | Day |
| 6,352,851 | B1 | 3/2002 | Nielsen et al. |
| 6,361,809 | B1 | 3/2002 | Christophersen et al. |
| 7,244,597 | B2 * | 7/2007 | Veit et al. ..................... 435/161 |
| 7,354,752 | B2 | 4/2008 | Dunn-Coleman et al. |
| 7,413,887 | B2 | 8/2008 | Dunn-Coleman et al. |
| 7,429,476 | B2 | 9/2008 | Clarkson et al. |
| 2006/0094080 | A1 * | 5/2006 | Dunn-Coleman et al. ... 435/69.1 |
| 2007/0298145 | A1 | 12/2007 | Miasnikov et al. |
| 2008/0220498 | A1 * | 9/2008 | Cervin et al. .................. 435/195 |

FOREIGN PATENT DOCUMENTS

| | | | |
|---|---|---|---|
| EP | 0 473 545 A2 | | 3/1992 |
| WO | WO 84/02921 A2 | | 8/1984 |
| WO | WO 92/00381 A1 | | 1/1992 |
| WO | WO 92/06209 A1 | | 4/1992 |
| WO | WO 95/13362 A1 | | 5/1995 |
| WO | WO 97/20920 A1 | | 6/1997 |
| WO | WO 99/28488 A2 | | 6/1999 |
| WO | WO 00/04136 A1 | | 1/2000 |
| WO | WO 02/38787 | * | 5/2002 |
| WO | WO 2004/111218 A2 | | 12/2004 |
| WO | WO 2005/052148 A2 | | 6/2005 |
| WO | WO 2006/043178 | * | 4/2006 |
| WO | WO 2006/043178 A2 | | 4/2006 |
| WO | WO 2007/144424 A | | 12/2007 |
| WO | WO 2008/021050 A | | 2/2008 |
| WO | WO 2008/097619 A | | 8/2008 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Martinez-Amezcua et al., Poultry Science 85:470-475, 2006.*
Altschul, S.F. et al. "Local alignment statistics." *Methods Enzymol* 266:460-80, 1996.
Altschul, S.F. et al. "Basic local alignment search tool." *J. Mol. Biol.* 215(3):403-410, 1990.
Boel, E. et al. "Glucoamylases G1 and G2 from *Aspergillus niger* are synthesized from two different but closely related mRNAs." *The EMBO Journal* 3(5):1097-1102, 1984.
Chen, H.M. et al. "Substitution of asparagine residues in *Aspergillus awamori* glucoamylase by site-directed mutagenesis to eliminate N-glycosylation and inactivation by deamidation." *Biochem. J.* 301(Pt 1):275-281, 1994.
Chen, H.-M. et al. "Identification and elimination by site-directed mutagenesis of thermolabile aspartyl bonds in *Aspergillus awamori* glucoamylase." *Protein Eng.* 8(6):575-582, 1995.
Chen, H.-M. et al. "Effect of replacing helical glycine residues with alanines on reversible and irreversible stability and production of *Aspergillus awamori* glucoamylase." *Protein Eng.* 9(6):499-505, 1996.
Fiske, C.H. et al. "The Colorimetric Determination of Phosphorus." *J. Biol. Chem* 66:375-400, 1925.
Hata, Y. et al. "The glucoamylase cDNA from *Aspergillus oryzae*: its cloning, nucleotide sequence, and expression in *Saccharomyces cerevisiae*." *Agric. Biol. Chem.* 55(4):941-9, 1991.
Jensen, B. et al. "Purification of extracellular amylolytic enzymes from the thermophilic fungus *Thermomyces lanuginosus*." *Can. J. Microbiol.* 34(3):218-223, 1988.
Keim, C.R. "The wet milling process: the basis for corn wet milling alcohol production." In *The Alcohol Textbook: A reference for the beverage, fuel and industrial alcohol industries*, eds. K. Jacques et al. Nottingham, UK: Nottingham UP, pp. 39-48, 1999.

(Continued)

*Primary Examiner* — Delia Ramirez
(74) *Attorney, Agent, or Firm* — Danisco US Inc.

(57) ABSTRACT

Described are compositions and methods relating to the use of a glucoamylase in combination with a phytase in starch processing to reduce the levels of phytic acid in end-products.

20 Claims, 1 Drawing Sheet

OTHER PUBLICATIONS

Kelsall, D.R. et al. "Grain dry milling and cooking for alcohol production: designing for 23% ethanol and maximum yield." In *The Alcohol Textbook: A reference for the beverage, fuel and industrial alcohol industries*, eds. K. Jacques et al. Nottingham, UK: Nottingham UP, pp. 7-23, 1999.

Needleman, S.B. et al. "A general method applicable to the search for similarities in the amino acid sequence of two proteins." *J. Mol. Biol* 48(3):443-53, 1970.

Pearson, W.R. et al. "Improved Tools for Biological Sequence Comparison." *Proc. Natl. Acad. Sci. USA* 85(8):2444-2448, 1988.

Shpaer, E.G. "GeneAssist: Smith-Waterman and other database similarity searches and identification of motifs." In *Sequence Data Analysis Guidebook*, Methods in Molecular Biology, No. 70, Totowa, NJ: Humana Press, pp. 173-187, 1997.

Smith, T.F. et al. "Comparison of biosequences." *Adv. Appl. Math* 2:482-489, 1981.

Takahashi, T. et al. "Different Behavior towards Raw Starch of Three Forms of Glucoamylase from a *Rhizopus* Sp." *J Biochem* 98(3):663-671, 1985.

Taylor, P.M. et al. "Some Properties of a Glucoamylase Produced by the Thermophilic Fungus *Humicola lanuginosa*." *Carbohydrate Research* 61:301-308, 1978.

International Search Report for International Application No. PCT/US2009/036477, mailed Aug. 20, 2009.

Hruby et al. "Phytase in ethanol production process improves nutritive value of DDGS", Poultry Science (Supplement 1), vol. 86, 2007, p. 397.

\* cited by examiner

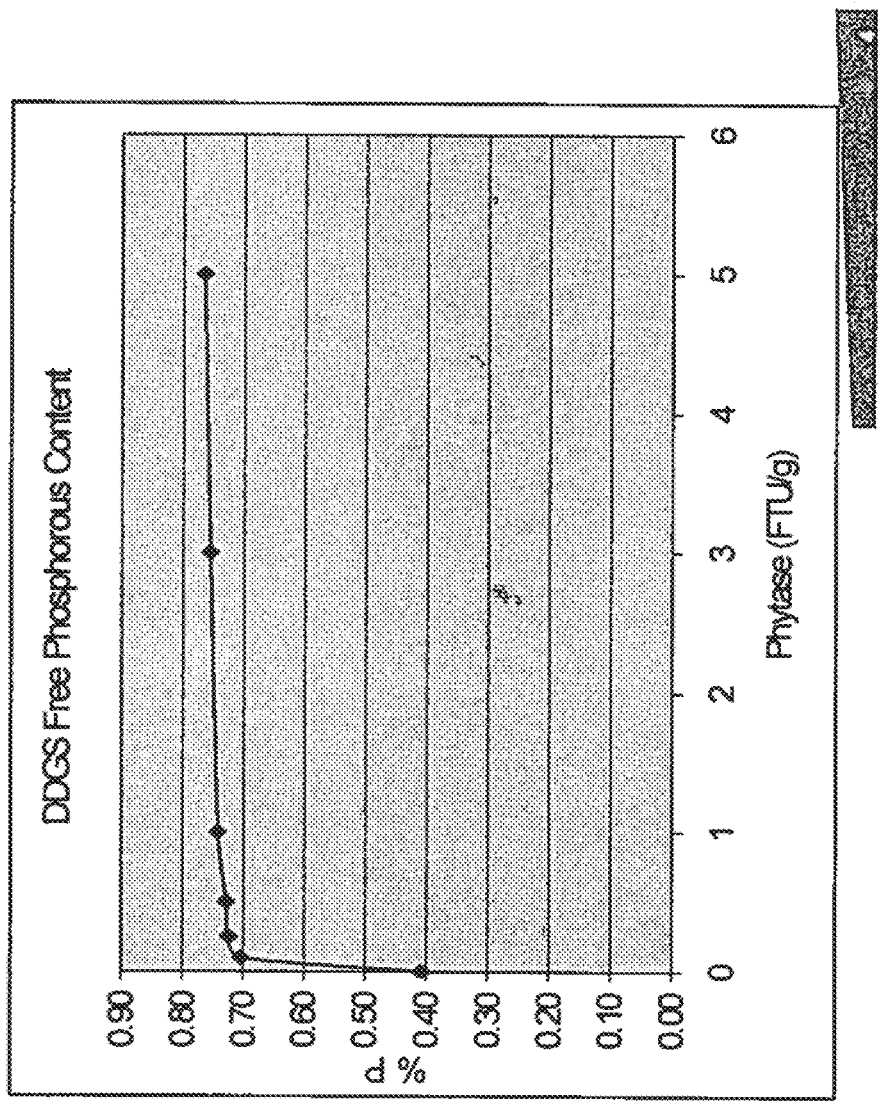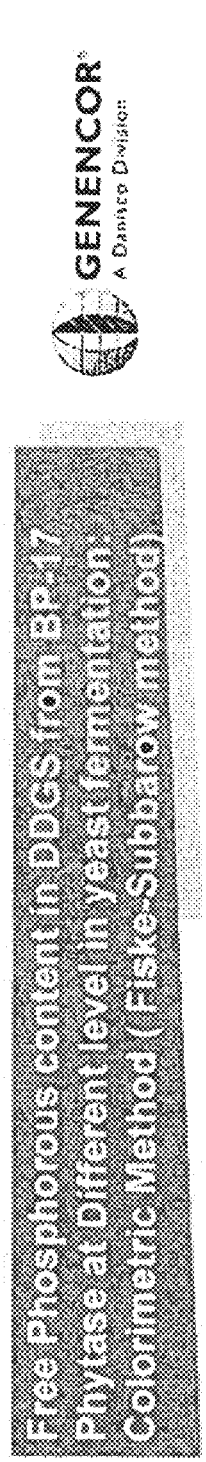

SEQUENCE LISTING

```
<160> NUMBER OF SEQ ID NOS: 8

<210> SEQ ID NO 1
<211> LENGTH: 599
<212> TYPE: PRT
<213> ORGANISM: Trichoderma reesei
<220> FEATURE:
<221> NAME/KEY: misc_feature
<223> OTHER INFORMATION: Sequence of Trichoderma reesei glucoamylase
      (TrGA)

<400> SEQUENCE: 1

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Ile Asp Pro Asp Tyr Tyr
            35                  40                  45

Tyr Met Trp Thr Arg Asp Ser Ala Leu Val Phe Lys Asn Leu Ile Asp
        50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Val Asp Ser
```

```
                275                 280                 285
Phe Arg Ser Ile Tyr Gly Val Asn Lys Gly Ile Pro Ala Gly Ala Ala
290                 295                 300
Val Ala Ile Gly Arg Tyr Ala Glu Asp Val Tyr Tyr Asn Gly Asn Pro
305                 310                 315                 320
Trp Tyr Leu Ala Thr Phe Ala Ala Glu Gln Leu Tyr Asp Ala Ile
                325                 330                 335
Tyr Val Trp Lys Lys Thr Gly Ser Ile Thr Val Thr Ala Thr Ser Leu
                340                 345                 350
Ala Phe Phe Gln Glu Leu Val Pro Gly Val Thr Ala Gly Thr Tyr Ser
                355                 360                 365
Ser Ser Ser Ser Thr Phe Thr Asn Ile Ile Asn Ala Val Ser Thr Tyr
                370                 375                 380
Ala Asp Gly Phe Leu Ser Glu Ala Ala Lys Tyr Val Pro Ala Asp Gly
385                 390                 395                 400
Ser Leu Ala Glu Gln Phe Asp Arg Asn Ser Gly Thr Pro Leu Ser Ala
                405                 410                 415
Leu His Leu Thr Trp Ser Tyr Ala Ser Phe Leu Thr Ala Thr Ala Arg
                420                 425                 430
Arg Ala Gly Ile Val Pro Pro Ser Trp Ala Asn Ser Ser Ala Ser Thr
                435                 440                 445
Ile Pro Ser Thr Cys Ser Gly Ala Ser Val Val Gly Ser Tyr Ser Arg
450                 455                 460
Pro Thr Ala Thr Ser Phe Pro Ser Gln Thr Pro Lys Pro Gly Val
465                 470                 475                 480
Pro Ser Gly Thr Pro Tyr Thr Pro Leu Pro Cys Ala Thr Pro Thr Ser
                485                 490                 495
Val Ala Val Thr Phe His Glu Leu Val Ser Thr Gln Phe Gly Gln Thr
                500                 505                 510
Val Lys Val Ala Gly Asn Ala Ala Ala Leu Gly Asn Trp Ser Thr Ser
                515                 520                 525
Ala Ala Val Ala Leu Asp Ala Val Asn Tyr Ala Asp Asn His Pro Leu
                530                 535                 540
Trp Ile Gly Thr Val Asn Leu Glu Ala Gly Asp Val Val Glu Tyr Lys
545                 550                 555                 560
Tyr Ile Asn Val Gly Gln Asp Gly Ser Val Thr Trp Glu Ser Asp Pro
                565                 570                 575
Asn His Thr Tyr Thr Val Pro Ala Val Ala Cys Val Thr Gln Val Val
                580                 585                 590
Lys Glu Asp Thr Trp Gln Ser
                595

<210> SEQ ID NO 2
<211> LENGTH: 453
<212> TYPE: PRT
<213> ORGANISM: Trichoderma reesei
<220> FEATURE:
<221> NAME/KEY: misc_feature
<223> OTHER INFORMATION: Catalytic domain of TrGA corresponding to
      residues 1-453 of SEQ ID NO: 1

<400> SEQUENCE: 2

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
                20                  25                  30
```

```
Ala Gly Ala Val Ile Ala Ser Pro Ser Thr Ile Asp Pro Asp Tyr Tyr
             35                  40                  45

Tyr Met Trp Thr Arg Asp Ser Ala Leu Val Phe Lys Asn Leu Ile Asp
     50                  55                  60

Arg Phe Thr Glu Thr Tyr Asp Ala Gly Leu Gln Arg Arg Ile Glu Gln
 65                  70                  75                  80

Tyr Ile Thr Ala Gln Val Thr Leu Gln Gly Leu Ser Asn Pro Ser Gly
                 85                  90                  95

Ser Leu Ala Asp Gly Ser Gly Leu Gly Glu Pro Lys Phe Glu Leu Thr
                100                 105                 110

Leu Lys Pro Phe Thr Gly Asn Trp Gly Arg Pro Gln Arg Asp Gly Pro
            115                 120                 125

Ala Leu Arg Ala Ile Ala Leu Ile Gly Tyr Ser Lys Trp Leu Ile Asn
        130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Asp Ser
        275                 280                 285

Phe Arg Ser Ile Tyr Gly Val Asn Lys Gly Ile Pro Ala Gly Ala Ala
    290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
        355                 360                 365

Ser Ser Ser Ser Thr Phe Thr Asn Ile Ile Asn Ala Val Ser Thr Tyr
370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
        435                 440                 445

Ile Pro Ser Thr Cys
450
```

<210> SEQ ID NO 3
<211> LENGTH: 38
<212> TYPE: PRT
<213> ORGANISM: Trichoderma reesei
<220> FEATURE:
<221> NAME/KEY: misc_feature
<223> OTHER INFORMATION: Linker region of TrGA corresponding to residues
      453-491 of SEQ ID NO: 1

<400> SEQUENCE: 3

Ser Gly Ala Ser Val Val Gly Ser Tyr Ser Arg Pro Thr Ala Thr Ser
1               5                   10                  15

Phe Pro Pro Ser Gln Thr Pro Lys Pro Gly Val Pro Ser Gly Thr Pro
                20                  25                  30

Tyr Thr Pro Leu Pro Cys
            35

<210> SEQ ID NO 4
<211> LENGTH: 108
<212> TYPE: PRT
<213> ORGANISM: Trichoderma reesei
<220> FEATURE:
<221> NAME/KEY: misc_feature
<223> OTHER INFORMATION: Starch binding domain of TrGA corresponding to
      residues 492-599 of SEQ ID NO: 1

<400> SEQUENCE: 4

Ala Thr Pro Thr Ser Val Ala Val Thr Phe His Glu Leu Val Ser Thr
1               5                   10                  15

Gln Phe Gly Gln Thr Val Lys Val Ala Gly Asn Ala Ala Ala Leu Gly
                20                  25                  30

Asn Trp Ser Thr Ser Ala Ala Val Ala Leu Asp Ala Val Asn Tyr Ala
            35                  40                  45

Asp Asn His Pro Leu Trp Ile Gly Thr Val Asn Leu Glu Ala Gly Asp
        50                  55                  60

Val Val Glu Tyr Lys Tyr Ile Asn Val Gly Gln Asp Gly Ser Val Thr
65                  70                  75                  80

Trp Glu Ser Asp Pro Asn His Thr Tyr Thr Val Pro Ala Val Ala Cys
                85                  90                  95

Val Thr Gln Val Val Lys Glu Asp Thr Trp Gln Ser
            100                 105

<210> SEQ ID NO 5
<211> LENGTH: 413
<212> TYPE: PRT
<213> ORGANISM: Buttiauxiella spp.
<220> FEATURE:
<221> NAME/KEY: misc_feature
<223> OTHER INFORMATION: Mature protein sequence of Buttiauxella phytase

<400> SEQUENCE: 5

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
            85                  90                  95

Lys Thr Gly Glu Ala Phe Leu Ala Gly Leu Ala Pro Gln Cys Gly Leu
        100                 105                 110

Thr Ile His His Gln Gln Asn Leu Glu Lys Ala Asp Pro Leu Phe His
    115                 120                 125

Pro Val Lys Ala Gly Thr Cys Ser Met Asp Lys Thr Gln Val Gln Gln
130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 6
<211> LENGTH: 413
<212> TYPE: PRT
<213> ORGANISM: Buttiauxiella spp.
<220> FEATURE:
<221> NAME/KEY: misc_feature
<223> OTHER INFORMATION: Mature protein sequence of Buttiauxiella phytase
      variant D92A

<400> SEQUENCE: 6

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg

-continued

```
                    20                  25                  30
Asp Val Thr Pro Asn Thr Trp Pro Glu Trp Pro Val Lys Leu Gly Tyr
                35                  40                  45
Ile Thr Pro Arg Gly Glu His Leu Ile Ser Leu Met Gly Gly Phe Tyr
        50                  55                  60
Arg Gln Lys Phe Gln Gln Gln Gly Ile Leu Ser Gln Gly Ser Cys Pro
 65                  70                  75                  80
Thr Pro Asn Ser Ile Tyr Val Trp Ala Asp Val Ala Gln Arg Thr Leu
                85                  90                  95
Lys Thr Gly Glu Ala Phe Leu Ala Gly Leu Ala Pro Gln Cys Gly Leu
            100                 105                 110
Thr Ile His His Gln Gln Asn Leu Glu Lys Ala Asp Pro Leu Phe His
            115                 120                 125
Pro Val Lys Ala Gly Thr Cys Ser Met Asp Lys Thr Gln Val Gln Gln
            130                 135                 140
Ala Val Glu Lys Glu Ala Gln Thr Pro Ile Asp Asn Leu Asn Gln His
145                 150                 155                 160
Tyr Ile Pro Phe Leu Ala Leu Met Asn Thr Thr Leu Asn Phe Ser Thr
                165                 170                 175
Ser Ala Trp Cys Gln Lys His Ser Ala Asp Lys Ser Cys Asp Leu Gly
            180                 185                 190
Leu Ser Met Pro Ser Lys Leu Ser Ile Lys Asp Asn Gly Asn Lys Val
            195                 200                 205
Ala Leu Asp Gly Ala Ile Gly Leu Ser Ser Thr Leu Ala Glu Ile Phe
            210                 215                 220
Leu Leu Glu Tyr Ala Gln Gly Met Pro Gln Ala Ala Trp Gly Asn Ile
225                 230                 235                 240
His Ser Glu Gln Glu Trp Ala Ser Leu Leu Lys Leu His Asn Val Gln
                245                 250                 255
Phe Asp Leu Met Ala Arg Thr Pro Tyr Ile Ala Arg His Asn Gly Thr
            260                 265                 270
Pro Leu Leu Gln Ala Ile Ser Asn Ala Leu Asn Pro Asn Ala Thr Glu
            275                 280                 285
Ser Lys Leu Pro Asp Ile Ser Pro Asp Asn Lys Ile Leu Phe Ile Ala
            290                 295                 300
Gly His Asp Thr Asn Ile Ala Asn Ile Ala Gly Met Leu Asn Met Arg
305                 310                 315                 320
Trp Thr Leu Pro Gly Gln Pro Asp Asn Thr Pro Pro Gly Gly Ala Leu
                325                 330                 335
Val Phe Glu Arg Leu Ala Asp Lys Ser Gly Lys Gln Tyr Val Ser Val
            340                 345                 350
Ser Met Val Tyr Gln Thr Leu Glu Gln Leu Arg Ser Gln Thr Pro Leu
            355                 360                 365
Ser Leu Asn Gln Pro Ala Gly Ser Val Gln Leu Lys Ile Pro Gly Cys
            370                 375                 380
Asn Asp Gln Thr Ala Glu Gly Tyr Cys Pro Leu Ser Thr Phe Thr Arg
385                 390                 395                 400
Val Val Ser Gln Ser Val Glu Pro Gly Cys Gln Leu Gln
                405                 410

<210> SEQ ID NO 7
<211> LENGTH: 413
<212> TYPE: PRT
<213> ORGANISM: Buttiauxiella spp.
<220> FEATURE:
```

<221> NAME/KEY: misc_feature
<223> OTHER INFORMATION: Mature protein sequence of Buttiauxella phytase variant BP-11

<400> SEQUENCE: 7

```
Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gly Ile Leu Ser Gln Gly Ser Cys Pro
65                  70                  75                  80

Thr Pro Asn Ser Ile Tyr Val Trp Thr Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400
```

```
Val Val Ser Gln Ser Val Glu Pro Gly Cys Gln Leu Gln
            405                 410
```

```
<210> SEQ ID NO 8
<211> LENGTH: 413
<212> TYPE: PRT
<213> ORGANISM: Buttiauxiella spp.
<220> FEATURE:
<221> NAME/KEY: misc_feature
<223> OTHER INFORMATION: Mature protein sequence of Buttiauxella phytase
      variant BP-17

<400> SEQUENCE: 8

Asn Asp Thr Pro Ala Ser Gly Tyr Gln Val Glu Lys Val Val Ile Leu
 1               5                  10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
```

```
                       340                 345                 350
Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410
```

GLUCOAMYLASE AND *BUTTIAUXIELLA* PHYTASE DURING SACCHARIFICATION

PRIORITY

The present application claim priority to U.S. Provisional Patent Application Ser. No. 61/035,672, filed on Mar. 11, 2008, which is hereby incorporated by reference in its entirety.

TECHNICAL FIELD

The described methods relate to the use of glucoamylase and a *Buttiauxella* spp. phytase in a starch conversion processes, e.g., for the production of DDGS for animal feed or in fermentation processes for producing organic compounds such as ethanol.

BACKGROUND

Industrial fermentation methods predominantly use glucose as a feedstock for the production of a multitude of end-products, including enzymes, proteins, amino acids, organic acids, sugar alcohols, pharmaceuticals and other biochemicals. In many applications glucose is produced from the enzymatic conversion of substrates comprising starch and cellulose (e.g., whole milled cereal grains). The processing of starch to produce glucose generally involves two steps, namely liquefaction of granular starch and saccharification of the liquefied starch to produce glucose. Further steps may include purification and isomerization, e.g., when the desired end-product is a purified dextrose or fructose, or fermentation and distillation, e.g., when the desired end-product is an alcohol (e.g., ethanol).

Liquefaction converts a slurry of starch polymer granules into a solution of shorter chain length dextrins of lower viscosity. The saccharification step further converts those shorter-chain dextrins into glucose. Commonly, the starch is liquefied by exposure to an elevated temperature and enzymatic bioconversion. A common enzymatic liquefaction process involves adding a thermostable bacterial alpha (α)-amylase (e.g., SPEZYME® FRED or SPEZYME® XTRA (Danisco US, Inc, Genencor Division) or TERMAMYL® SC or TERMAMYL™120L (Novozymes)) to a slurry comprising a substrate that includes granular starch. The pH is adjusted to between 5.5 to 6.5 and the temperature is elevated to greater than 90° C. The starch is first gelatinized and then exposed to the saccharifying enzymes. Typically, saccharification takes place in the presence of glucoamylase enzymes such as glucoamylase from *Aspergillus niger* (e.g., OPTI-DEX® L-400 (Danisco US, Inc. Genencor Division)) at a more acidic pH than that used in the liquefaction step. The pH of a typical saccharification step is around pH 4.0 to 5.0. The resulting sugars are then fermented to provide the desired end-products (i.e., ethanol). In the process of producing ethanol, side-products and waste-products such as distillers dried grains and solubles (DDGS) are produced and used for feed. Further, the resulting liquid from the process (i.e., the thin stillage) is recycled by mixing it with slurry.

A number of variations exist for the liquefaction and saccharification of a starch substrate. However, a need continues to exist for advances in starch liquefaction, saccharification, and fermentation.

BRIEF SUMMARY

Described are compositions and methods involving the use of a glucoamylase in combination with a phytase in a starch conversion process. Such a process may be used for the production of organic compounds such as ethanol, the production of DDGS for animal feed, or both. In some embodiments, the compositions and methods comprise adding an enzyme blend comprising a glucoamylase, and phytase to a starch conversion processes during pre-saccharification, saccharification, and/or combined saccharification/fermentation. Such compositions and methods provide certain advantages over the use of a glucoamylase alone.

In some aspects, the invention provides methods for fermenting a starch, comprising adding to a composition to be saccharified in any order a combination of at least one glucoamylase, and at least one *Buttiauxella* spp. phytase. In some embodiments, the at least one glucoamylase and at least one *Buttiauxella* spp. phytase are added to a composition that has undergone liquefaction. In other aspects, the starch is fermented to ethanol. In other aspects, DDGS are produced that have reduced phytic acid. In other aspects, DDGS are produced that comprise active phytase. In some further aspects, thin stillage is produced and has reduced phytase. In some embodiments, the thin stillage is recycled into the process. In some aspects, methods of producing an alcohol are provided, including contacting a slurry comprising a starch substrate with at least one α-amylase producing oligosaccharides, contacting the oligosaccharides with at least one glucoamylase and at least one phytase, wherein the phytase is obtained from a *Buttiauxella* spp., to produce fermentable sugars; and fermenting the fermentable sugars in the presence of a fermenting organism to produce alcohol. In some embodiments, the contacting and occur simultaneously. In some embodiments, the temperature can be raised above the gelatinization temperature of the starch substrate after the treatment with the alpha amylase and before adding the glucoamylase.

In some embodiments, the starch substrate is a milled grain and the milled grain is chosen from maize, barley, wheat, rice, sorghum, rye, millet, and/or triticale. In some embodiments, the at least one glucoamylase has at least 90% sequence identity to the sequence of SEQ ID NO: 5. In some embodiments, the phytase also has an alanine at amino acid 92 and/or at least one of the following amino acids: a thiamine at position 89, an isoleucine at position 134, a serine at position 164, a lysine at position 176, a proline at position 178, a glutamic acid at position 207, a serine at position 209, a leucine at position 248, a tyrosine at position 256, a glutamic acid at position 261, and a lysine at position 270. In some embodiments, the phytase has at least one of the following amino acid changes: A89T, D92A, T134I, F164S, T176K, A178P, K207E, A209S, S248L, Q256Y, A261E, and N270K. In some embodiments, the phytase is wild-type *Buttiauxella* spp., phytase (BP-WT) or a variant selected from BP-11 and BP-17. In some embodiments, the phytase has the amino acid sequence set forth in any of SEQ ID NOs: 5, 6, 7, and 8.

In some embodiments, the method also includes contacting the oligosaccharides with at least one other/additional enzyme chosen from an α-amylase, a second glucoamylase, a second phytase, a cellulose, a pullulanase, a protease, and/or a laccase. The alcohol can be ethanol. In some embodiments, the method includes recovering the alcohol. In some embodiments, the method can also include recovering DDGS.

Other aspects of the invention include methods for reducing phytic acid during ethanol fermentation by contacting a slurry including a starch substrate, with at least one α-amylase to produce a liquefact, contacting the liquefact with at least one glucoamylase and at least one phytase, wherein the phytase has at least 90% amino acid sequence identity to SEQ ID NO: 5 and wherein the phytase has an alanine at position 92, under conditions such that fermentable sugars are produced; and fermenting the fermentable sugars in the presence of a fermenting organism under conditions such that ethanol and/or DDGS are produced. In some embodiments, the method includes raising the temperature above the liquefaction temperature for the starch substrate. In some embodiments, contacting the starch substrate with at least one glucoamylase and at least one phytase and fermenting the fermentable sugars in the presence of a fermenting organism occur simultaneously.

In some embodiments, the method includes recovering the ethanol and/or DDGS. In some embodiments, the glucoamylase is from a filamentous fungus chosen from *Trichoderma, Penicillium, Taleromyces, Aspergillus,* and/or *Humicola*. In some embodiments, the *Trichodema* is *Trichoderma reesei*. In some embodiments, the phytase is BP-17. In some embodiments, the DDGS have active residual phytase. The DDGS can be blended into a feed. In some embodiments, when the DDGS are blended with grains or feed to produce an animal feed, the active phytase reduces the phytic acid in the feed. In some embodiments, the starch substrate is a milled grain, such as maize, barley, millet, wheat, rice, sorghum, rye, and/or triticale.

Further aspects of the invention include a method of reducing phytic acid in DDGS, by contacting a slurry comprising a starch substrate with at least one α-amylase; contacting the starch substrate with at least one *Trichoderma reesei* glucoamylase (TrGA) and at least one phytase, wherein the phytase has at least 90% amino acid sequence identity to SEQ ID NO: 5 under conditions such that fermentable sugars are produced; and fermenting the fermentable sugars in the presence of a fermenting organism to produce ethanol and/or DDGS. In some embodiments, contacting the starch substrate with at least one glucoamylase and at least one phytase and fermenting the fermentable sugars in the presence of a fermenting organism occur simultaneously. In some embodiments, the phytase has at least 95% sequence identity with the phytase of SEQ ID NO: 5 and has an alanine at amino acid 92. In some embodiments, the phytase is wild-type *Buttiauxella* spp., phytase (BP-WT) or a variant selected from BP-11 and BP-17.

Also contemplated is a single composition comprising a blend of a glucoamylase in combination with a phytase. Such a blend may be added during the pre-saccharification, saccharification, and/or combined saccharification/fermentation steps of a starch conversion process.

These and other aspects of the present compositions and methods are described in greater detail, below.

BRIEF DESCRIPTION OF THE DRAWINGS

FIG. 1 shows the free phosphorus content in DDGS obtained using an enzyme composition including BP-17 phytase at different levels in a yeast fermentation of corn.

BRIEF DESCRIPTION OF THE SEQUENCES

SEQ ID NO: 1 is the amino acid sequence of *Trichoderma reesei* glucoamylase (TrGA).

SEQ ID NO: 2 is the amino acid sequence of the catalytic domain of TrGA corresponding to residues 1-453.

SEQ ID NO: 3 is the amino acid sequence of the linker region of TrGA corresponding to residues 453-491.

SEQ ID NO: 4 is the amino acid sequence of the starch binding domain of TrGA corresponding to residues 492-599.

SEQ ID NO: 5 is the amino acid sequence of the mature protein sequence of *Buttiauxella* phytase.

SEQ ID NO: 6 is the amino acid sequence of the mature protein sequence of *Buttiauxella* phytase variant D92A.

SEQ ID NO: 7 is the amino acid sequence of the mature protein sequence of *Buttiauxella* phytase variant BP-11.

SEQ ID NO: 8 is the amino acid sequence of the mature protein sequence of *Buttiauxella* phytase variant BP-17.

DETAILED DESCRIPTION

I. Introduction

The present compositions and methods relate to an enzyme blend including a glucoamylase in combination with at least one phytase for use in a starch conversion processes, e.g., for the production of DDGS for animal feed or in a fermentation processes for producing organic compounds such as ethanol. The compositions and methods may be used for the reduction of phytic acid during saccharification, fermentation and/or simultaneous saccharification and fermentation (SSF), resulting in a reduction in phytic acid in the products or by-products of the fermentation (e.g., the DDGS and the thin stillage).

In some embodiments, the phytase is *Buttiauxella* spp, phytase or variant thereof. In some embodiments, the phytase has at least 90% sequence identity to SEQ ID NO: 5, including at least 91%, at least 92%, at least 93%, at least 94%, at least 95%, at least 96%, at least 97%, at least 98%, at least 99%, and up to and including 100%. In some embodiments, the phytase has at least 90% sequence identity to SEQ ID NO: 5, including at least 91%, at least 92%, at least 93%, at least 94%, at least 95%, at least 96%, at least 97%, at least 98%, at least 99%, and up to and including 100%, and further includes an alanine at position 92. In some embodiments, the phytase has at least 90% sequence identity to SEQ ID NO: 5, including at least 91%, at least 92%, at least 93%, at least 94%, at least 95%, at least 96%, at least 97%, at least 98%, at least 99%, and up to and including 100%, further includes an alanine at position 92, and additionally has at least one of the following amino acid sequence features: a threonine at position 89, an isoleucine at position 134, a serine at position 164, a lysine at position 176, a proline at position 178, a glutamic acid at position 207, a serine at position 209, a leucine at position 248, a tyrosine at position 256, a glutamic acid at position 261, and a lysine at position 270. In some embodiments, the phytase has at least one of the following amino acid substitutions: A89T, T134I, F164S, T176K, A178P, K207E, A209S, S248L, Q256Y, A261E, and N270K, with or without the additional substitution D92A. In some embodiments, the phytase is wild-type *Buttiauxella* phytase or variant BP-11 or BP-17. In some embodiments, the variant phytase has phytase activity of a least about 50%, including at least 60%, at least 70%, at least 80%, at least 90%, at least 95%, and even at least 97% of that of *Buttiauxella* phytase.

In some embodiment, the glucoamylase is obtained from a filamentous fungus. In particular embodiments, the glucoamylase has at least about 90% sequence identity to *Trichoderma reesei* glucoamylase (TrGA; SEQ ID NO: 1), including at least 91%, at least 92%, at least 93%, at least 94%, at least 95%, at least 96%, at least 97%, at least 98%, at least 99%, and up to 100%.

These and other features of the present compositions and methods are described in more detail, below.

II. Definitions

Unless otherwise indicated, making and using the present compositions and methods involves conventional techniques commonly used in molecular biology, protein engineering, recombinant DNA techniques, microbiology, cell biology, cell culture, transgenic biology, immunology, and protein purification. Such techniques are known to those with skill in the art and are described in numerous texts and reference works. Although particular methods and materials are exemplified, similar or equivalent methods and materials can be used to make or use the compositions and methods.

Unless defined otherwise, all technical and scientific terms should be accorded their ordinary meaning. The following terms are defined for clarity:

"Alpha amylases" are α-1,4-glucan-4-glucanohydrolases (E.C. 3.2.1.1) having the ability to cleave or hydrolyze internal α-1,4-glycosidic linkages in starch (e.g., amylopectin or amylose polymers).

The terms "granular starch hydrolyzing (GSH) enzyme" and "enzymes having granular starch hydrolyzing (GSH) activity" refer to enzymes that have the ability to hydrolyze starch in granular form.

The term "functional equivalent" refers to a molecule, e.g., an enzyme, that has the same functional characteristics (such as enzymatic activity) of another molecule.

The term "variant," when used with reference to an enzyme (e.g., an α-amylase, a glucoamylase, an acid fungal protease, a phytase, or the like), refers to an enzyme derived from a parent enzyme but having a substitution, insertion, or deletion of one or more amino acids as compared to the parent enzyme. The term also includes hybrid forms of the enzyme, wherein, for example, the enzyme may have a C-terminus derived from one Bacillus spp. (e.g., B. licheniformis) and an N-terminus derived from a different Bacillus spp. (e.g., B. stearothermophilus), or vice versa. A variant may have one or more altered properties compared to the parent enzyme such as increased thermal stability, increased proteolytic stability, increase specific activity, broader substrate specificity, broader activity over a pH range, resistance to inhibition (e.g., substrate), or combinations thereof. A "parent enzyme" refers to an enzyme that is used as a starting point for modifications. A parent enzyme may be a naturally-occurring or "wild-type" enzyme.

As used herein "liquefaction" or "to liquefy" refers to a process by which starch is converted to shorter-chain, less-viscous dextrins.

As used herein, "dextrins" refer to short chain polymers of glucose (e.g., 2 to 10 units).

As used herein, the term "starch" refers to any material comprised of the complex polysaccharide carbohydrates (amylose and amylopectin) having the formula $(C_6H_{10}O_5)_x$, wherein x is any number.

As used herein, the term "granular starch" means raw starch, i.e., starch that has not been subject to a temperature at which gelatinization occurs.

As used herein, the terms "saccharifying enzyme" and "glucoamylase" are used interchangeably and refer to any enzyme that is capable of catalyzing the release of D-glucose from the non-reducing ends of starch and related oligosaccharides and polysaccharides.

As used herein, the term "oligosaccharide" refers to molecules having 2 to 10 monosaccharide units joined in glycosidic linkages. The monosaccharides may be glucose and/or other sugars. Oligosaccharides include dextrins and starch.

As used herein, the term "fermentable sugars" refers to sugars that are capable of being fermented by a fermenting organism. Fermentable sugars include, but are not limited to, oligosaccharides and dextrins.

As used herein, the term "dextrose equivalent" or "DE" refers to an industry standard for measuring the concentration of total reducing sugars, calculated as D-glucose on a dry weight basis. Unhydrolyzed granular starch has a DE that is essentially 0 and D-glucose has a DE of 100.

As used herein, the term "total sugar content" refers to the total sugar content present in a starch composition. The "total sugar content" can be measured at various times or points in a process.

As used herein, the term "dry solids" or "ds" refers to the total solids within a slurry expressed as a percentage on a dry weight basis.

As used herein, "percent (%) sequence identity" with respect to an amino acid or nucleotide sequence refers to the percentage of amino acid residues or nucleotides in a one sequence that are identical to the amino acid residues or nucleotides in another sequence, as determined by aligning the sequences and introducing gaps, where necessary, to achieve the best alignment (i.e., maximum percent sequence identity), and not considering conservative substitutions in determining sequence identity. Methods for performing sequence alignment and determining sequence identity are known and can be performed without undue experimentation to obtain definitive values. A number of algorithms are available for aligning sequences and determining sequence identity, including but not limited to: the homology alignment algorithm of Needleman et al., (1970) J. Mol. Biol. 48:443; the local homology algorithm of Smith et al., (1981) Adv. Appl. Math. 2:482; the search for similarity method of Pearson et al. (1988) Proc. Natl. Acad. Sci. USA 85:2444; the Smith-Waterman algorithm (1997) Meth. Mol. Biol. 70:173-187; BLASTP, BLASTN, and BLASTX algorithms (see Altschul et al., (1990) J. Mol. Biol. 215:403-410). Computerized programs using these algorithms are also available, and include, but are not limited to: ALIGN or Megalign (DNASTAR) software, or WU-BLAST-2 (see, e.g., Altschul et al. (1996) Meth. Enzym. 266:460-480); or GAP, BESTFIT, BLAST (e.g., Altschul et al., supra, FASTA, and TFASTA, available in the Genetics Computing Group (GCG) package, Version 8, Madison, Wis., USA); and CLUSTAL in the PC/Gene program by Intelligenetics, Mountain View, Calif., USA.

Those skilled in the art know how to determine appropriate parameters for measuring alignment, including algorithms needed to achieve maximal alignment over the length of the sequences being compared. In some embodiments, the sequence identity is determined using the default parameters determined by the program. In some embodiments, sequence identity can be determined by the Smith-Waterman homology search algorithm (see e.g., (1997) Meth. Mol. Biol. 70:173-187) as implemented in MSPRCH program (Oxford Molecular, Accelrys Ltd., Oxford England) using an affine gap search with the following search parameters: gap open penalty of 12, and gap extension penalty of 1. In some embodiments, paired amino acid comparisons can be carried out using the GAP program of the GCG sequence analysis software package of Genetics Computer Group, Inc., Madison, Wis., employing the blosum 62 amino acid substitution matrix, with a gap weight of 12 and a length weight of 2. In some embodiments, with respect to optimal alignment of two amino acid sequences, the contiguous segment of the variant amino acid sequence may have at least one additional amino acid residue or at least one deleted amino acid residue with respect to the reference amino acid sequence. The contiguous segment used for comparison to the reference amino acid sequence includes at least about 20 contiguous amino acid residues and can include at least about 30, at least about 40, at least about 50 or more amino acid residues. Corrections for increased sequence identity associated with inclusion of gaps in the derivative's amino acid sequence can be made by assigning gap penalties.

Sequence searches are typically carried out using the BLASTN program when evaluating a given nucleic acid sequence relative to nucleic acid sequences in the GEN-BANK® DNA Sequence database and other public databases. In some embodiments, the BLASTX program is preferred for searching nucleic acid sequences that have been translated in all reading frames against amino acid sequences in the GENBANK®Protein Sequences and other public databases. Both BLASTN and BLASTX are typically run using default parameters of an open gap penalty of 11.0, and an extended gap penalty of 1.0, and utilize the BLOSUM-62 matrix (see, e.g., Altschul et al. (1997)).

Alignments of selected sequences find use in determining % identity (a term that is used interchangeably herein with the term % homology) between two or more sequences. In some embodiments, the CLUSTAL-W program in MacVector version 6.5, operated with default parameters, including an open gap penalty of 10.0, an extended gap penalty of 0.1, and a BLOSUM 30 similarity matrix is used.

As used herein, the term "milled" refers to plant material that has been reduced in size, e.g., by grinding, crushing, fractionating or any other means of particle size reduction or selection. The term encompasses dry and wet milling. "Dry milling" refers to the milling of whole dry grain, while "wet milling" refers to a process whereby grain is first soaked (i.e., steeped) in water to soften the grain.

As used herein, the term "gelatinization" refers to the solubilization of a starch molecule, generally by cooking at an elevated temperature, to form a viscous suspension.

As used herein, the term "gelatinization temperature" refers to the temperature at which gelatinization of a starch-containing substrate begins. In some embodiments, this is the lowest temperature at which gelatinization of a starch containing substrate begins. The exact temperature of gelatinization depends on the specific form of starch present and may vary depending on factors such as plant species, environmental conditions, growth conditions, and other parameters.

As used herein, the term "below the gelatinization temperature" refers to a temperature that is less than the gelatinization temperature.

As used herein, the term "slurry" refers to an aqueous mixture comprising insoluble solids (e.g., granular starch).

As used herein, the term "fermentation" refers to the enzymatic breakdown of organic substances by microorganisms to produce simpler organic compounds. While fermentation occurs under anaerobic conditions it is not intended that the term be solely limited to strict anaerobic conditions, as fermentation also occurs in the presence of oxygen (e.g., under microaerophilic and other conditions).

As used herein, the phrase "simultaneous saccharification and fermentation" or "SSF" refers to a process in the production of an end-product in which a fermenting organism, such as an ethanol producing microorganism, and at least one enzyme, such as a saccharifying enzyme, are combined in the same process step in the same vessel.

As used herein, the term "thin stillage" means the liquid portion of stillage separated from the solids (e.g., by screening or centrifugation) which contains suspended fine particles and dissolved material. The term "backset" is generally used to mean recycled thin stillage.

As used herein, the term "end-product" refers to a carbon-source derived product which is enzymatically converted from a fermentable substrate. In some embodiments, the end-product is an alcohol (e.g., ethanol).

As used herein, the term "derived from" encompasses the terms "originated from," "obtained from," "obtainable from," and "isolated from."

As used herein the term "fermenting organism" refers to a microorganism or cell that is suitable for use in fermentation methods for directly or indirectly producing an end-product. In some embodiments, the fermentating organism is eukaryotic (e.g., fungi), while in others it is prokaryotic (e.g., bacteria).

As used herein the term "ethanol producer" or ethanol producing microorganism" refers to a fermenting organism that is capable of producing ethanol from a mono- or oligosaccharide.

As used herein, the terms "recovered," "isolated," and "separated" refer to a protein, cell, nucleic acid, or amino acid that is removed from at least one component with which it is naturally associated.

As used herein, the terms "protein" and "polypeptide" are used interchangeably to refer to a series of amino acid residue linked via peptide bonds. Both the conventional one-letter and three-letter codes for amino acid residues are used. The 3-letter code is in conformity with the IUPAC-IUB Joint Commission on Biochemical Nomenclature (JCBN). It is understood that a polypeptide can be encoded by more than one nucleotide sequence due to the degeneracy of the genetic code. Unless otherwise indicated amino acids are written left to right in amino to carboxy orientation.

As used herein, the term "phytase" refers to an enzyme which is capable of catalyzing the hydrolysis of esters of phosphoric acid, including phytate, and releasing inorganic phosphate and inositol. In some embodiments, in addition to phytate, the phytase is capable of hydrolyzing at least one of the inositol-phosphates of intermediate degrees of phosphorylation.

As used herein, the term "wild-type" refers to a naturally-occurring (native) polypeptide or polynucleotide. The term wild-type may, in some cases, be used interchangeably with the terms "parent" or "parent sequence."

As used herein, the terms "contacting" and "exposing" refer to placing at least one enzyme in sufficient proximity to its cognate substrate to enable the enzyme to convert the substrate to at least one end-product. The end-product may be a "product of interest" (i.e., an end-product that is the desired outcome of the fermentation reaction). "Contacting" includes mixing a solution comprising an enzyme with the cognate substrate.

As used herein, the singular terms "a," "an," and "the" includes the plural unless the context clearly indicates otherwise. Thus, for example, reference to a composition containing "a compound" includes a mixture of two or more compounds. The term "or" generally means "and/or," unless the content clearly dictates otherwise.

Headings are provided for convenience, and a description provided under one heading may apply equally to other parts of the disclosure. All recited species and ranges can be expressly included or excluded by suitable language or provisos.

Numeric ranges are inclusive of the numbers defining the range. Where a range of values is provided, it is understood that each intervening value between the upper and lower limits of that range is also specifically disclosed, to a tenth of the unit of the lower limit (unless the context clearly dictates otherwise). The upper and lower limits of smaller ranges may independently be included or excluded in the range.

All patents, patent applications, articles and publications mentioned herein, both supra and infra, are hereby expressly incorporated herein by reference.

III. Exemplary Embodiments

A. Glucoamylases

Various glucoamylases (GA) (E.C. 3.2.1.3) may be used in accordance with the present compositions and methods. In some embodiments, the GA are endogenously expressed by bacteria, plants, and/or fungi, while in other embodiments the GA are heterologous to the host cells (e.g., bacteria, plants and/or fungi). In some embodiments, the GA are produced by strains of filamentous fungi and yeast, e.g., commercially available GA produced by strains of *Aspergillus* and *Trichoderma*. Suitable GA include naturally occurring wild-type enzymes as well as variant and genetically engineered mutant enzyme, such as hybrid GA. Hybrid GA include those having a catalytic domain from a GA from one organism (e.g., *Talaromyces* GA) and a starch binding domain (SBD) from a GA from a different organism (e.g., *Trichoderma* GA). In some embodiments, the linker is included with the starch binding domain (SBD) or the catalytic domain. The following are exemplary GA suitable for use as described: *Aspergillus niger* G1 and G2 GA (see e.g., Boel et al. (1984) *EMBO J.* 3:1097-1102; WO 92/00381, WO 00/04136 and U.S. Pat. No. 6,352,851); *Aspergillus awamori* GA (see e.g., WO 84/02921); *Aspergillus oryzae* GA (see e.g., Hata et al. (1991) *Agric. Biol. Chem.* 55:941-949), and *Aspergillus shirousami* GA (see e.g., Chen et al. (1996) *Prot. Eng.* 9:499-505; Chen et al. (1995) *Prot. Eng.* 8:575-582; and Chen et al. (1994) *Biochem J.* 302:275-281).

Additional GA include those obtained from strains of *Talaromyces* (e.g., *T. emersonii, T. leycettanus, T. duponti* and *T. thermophilus* (see e.g., WO 99/28488; U.S. Pat. No. RE 32,153; U.S. Pat. No. 4,587,215); strains of *Trichoderma* (e.g., *T. reesei*); strains of *Rhizopus*, (e.g., *R. niveus* and *R. oryzae*); strains of *Mucor* and strains of *Humicola*, (e.g., *H. grisea* (see, e.g., Boel et al. (1984) *EMBO J.* 3:1097-1102; WO 92/00381; WO 00/04136; Chen et al. (1996) *Prot. Eng.* 9:499-505; Taylor et al. (1978) *Carbohydrate Res.* 61:301-308; U.S. Pat. Nos. 4,514,496, 4,092,434, and 4,618,579; Jensen et al. (1988) *Can. J. Microbiol.* 34:218-223; and SEQ ID NO: 3 of WO 2005/052148); as well as GA having at least about 80%, at least about 85%, at least about 90%, or at least about 95% sequence identity to SEQ ID NO: 4 disclosed in U.S. Pat. Pub. No. 2006-0094080.

In some embodiments, the GA has at least about 85%, at least about 90%, at least about 92%, at least about 94%, at least about 95%, at least about 96%, at least about 97%, at least about 98% and even at least about 99% sequence identity to the amino acid sequence of SEQ ID NO: 3 of WO 05/052148. Other GA useful in the present invention include those obtained from *Athelia rolfsii* and variants thereof (see, e.g., WO 04/111218) and *Penicillium* spp. (see, e.g., *Penicillium chrysogenum*).

Commercially available GA suitable for use as described include but are not limited to DISTILLASE®, OPTIDEX® L-400 and G ZYME® G990 4X, GC480, G-ZYME 480, FERMGEN® 1-400 (Danisco US, Inc, Genencor Division) CU.CONC® (Shin Nihon Chemicals, Japan), GLUCZYME (Amano Pharmaceuticals, Japan (see e.g. Takahashi et al. (1985) *J. Biochem.* 98:663-671)). Additional enzymes for use as described include three forms of GA (E.C.3.2.1.3) produced by a *Rhizopus* spp., namely "Gluc1" (MW 74,000), "Gluc2" (MW 58,600), and "Gluc3" (MW 61,400). Generally, any suitable GA can be used in accordance with the present composition and methods.

The mature amino acid sequence (SEQ ID NO: 1) of the *Trichoderma reesei* GA (TrGA) is shown below. The sequence has 599 amino acids, the catalytic domain (SEQ ID NO: 2) is underlined and corresponds to residues 1-453; the linker region (SEQ ID NO: 3) corresponds to residues 453-491; and the starch binding domain SEQ ID NO: 4 (in italics) corresponds to residues 492-599.

Mature Protein Sequence of *Trichoderma reesei* Glucoamylase (TrGA) (SEQ ID NO: 1)

```
  1 SVDDFISTET PIALNNLLCN VGPDGCRAFG TSAGAVIASP STIDPDYYYM
 51 WTRDSALVFK NLIDRFTETY DAGLQRRIEQ YITAQVTLQG LSNPSGSLAD
101 GSGLGEPKFE LTLKPFTGNW GRPQRDGPAL RAIALIGYSK WLINNNYQST
151 VSNVIWPIVR NDLNYVAQYW NQTGFDLWEE VNGSSFFTVA NQHRALVEGA
201 TLAATLGQSG SAYSSVAPQV LCFLQRFWVS SGGYVDSNIN TNEGRTGKDV
251 NSVLTSIHTF DPNLGCDAGT FQPCSDKALS NLKVVVDSFR SIYGVNKGIP
301 AGAAVAIGRY AEDVYYNGNP WYLATFAAAE QLYDAIYVWK KTGSITVTAT
351 SLAFFQELVF GVTAGTYSSS SSTFTNIINA VSTYADGFLS EAAKYVPADG
401 SLAEQFDRNS GTPLSALHLT WSYASFLTAT ARRAGIVEPS WANSSASTIP
451 STCSGASVVG SYSRPTATSF PPSQTPKPGV PSGTPYTPLP CATPTSVAVT
501 FHELVSTQFG QTVKVAGNAA ALGNWSTSAA VALDAVNYAD NHPLWIGTVN
551 LEAGDVVEYK YINVGQDGSV TWESDPNHTY TVPAVACVTQ VVKEDTWQS
```

In some embodiments, the GA has at least about 85%, at least about 90%, at least about 91%, at least about 92%, at least about 93%, at least about 94%, at least about 95%, at least about 96%, at least about 97%, at least about 98% and even at least about 99% sequence identity to the amino acid sequence of SEQ ID NOs: 1 or 2. In some embodiments, the GA is the TrGA disclosed in U.S. Pat. No. 7,413,887.

B. Phytases

Various phytases may be used in accordance with the present compositions and methods. Useful phytases include those capable of hydrolyzing phytic acid under the defined conditions of saccharification, fermentation and/or simultaneous saccharification and fermentation described herein. In some embodiments, the compositions and methods involve the addition of at least one phytase to a saccharification and/or SSF and the phytase is capable of liberating at least one inorganic phosphate from an inositol hexaphosphate (e.g., phytic acid).

Phytases can be grouped according to their preference for a specific position of the phosphate ester group on the phytate molecule at which hydrolysis is initiated, (e.g., as 3-phytases (EC 3.1.3.8) or as 6-phytases (EC 3.1.3.26)). In some embodiments, the phytase is that known as myo-inositol-hexakiphosphate-3-phosphohydrolase. However, it is intended that phytases from any suitable source (e.g., fungi and/or bacteria) will find use in the present compositions and methods.

In some embodiments, the phytase is obtained from a *Buttiauxiella* spp., such as *B. agrestis, B. brennerae, B. ferragutiase, B. gaviniae, B. izardii, B. noackiae*, or *B. warmboldiae*. Strains of *Buttiauxella* spp. are available from DSMZ, the German National Resource Center for Biological Material (Inhoffenstrabe 7B, 38124 Braunschweig, Germany) and other repositories. In some embodiments, the phytase is produced by *Buttiauxella* spp. strain P1-29 deposited under accession number NCIMB 41248.

In some embodiments, the phytase has at least about 75%, at least about 80%, at least about 85%, at least about 88%, at least about 90%, at least about 91%, at least about 92%, at least about 93%, at least about 94%, at least about 95%, at least about 96%, at least about 97%, at least about 98% and even at least about 99% sequence identity to *Buttiauxella* spp. phytase, having the amino acid sequence set forth in SEQ ID NO: 5.

Mature Protein Sequence of *Buttiauxella* Phytase (SEQ ID NO: 5)

```
NDTPASGYQV EKVVILSRHG VRAPTKMTQT MRDVTPNTWP

EWPVKLGYIT PRGEHLISLM GGFYRQKFQQ QGILSQGSCP

TPNSIYVWAD VDQRTLKTGE AFLAGLAPQC GLTIHHQQNL

EKADPLFHPV KAGTCSMDKT QVQQAVEKEA QTPIDNLNQH

YIPFLALMNT TLNFSTSAWC QKHSADKSCD LGLSMPSKLS

IKDNGNKVAL DGAIGLSSTL AEIFLLEYAQ GMPQAAWGNI

HSEQEWASLL KLHNVQFDLM ARTPYIARHN GTPLLQAISN

ALNPNATESK LPDISPDNKI LFIAGHDTNI ANIAGMLNMR

WTLPGQPDNT PPGGALVFER LADKSGKQYV SVSMVYQTLE

QLRSQTPLSL NQPAGSVQLK IPGCNDQTAE GYCPLSTFTR

VVSQSVEPGC QLQ
```

In some embodiments, the phytase has at least about 75%, at least about 80%, at least about 85%, at least about 88%, at least about 90%, at least about 91%, at least about 92%, at least about 93%, at least about 94%, at least about 95%, at least about 96%, at least about 97%, at least about 98% and even at least about 99% sequence identity to a variant of *Buttiauxella* spp. phytase having an alanine at amino acid 92, as set forth in SEQ ID NO: 6.

Mature Protein Sequence of *Buttiauxella* Phytase Variant D92A (SEQ ID NO: 6)

```
NDTPASGYQV EKVVILSRHG VRAPTKMTQT MRDVTPNTWP

EWPVKLGYIT PRGEHLISLM GGFYRQKFQQ QGILSQGSCP
```

```
TPNSIYVWAD VAQRTLKTGE AFLAGLAPQC GLTIHHQQNL

EKADPLFHPV KAGTCSMDKT QVQQAVEKEA QTPIDNLNQH

YIPFLALMNT TLNFSTSAWC QKHSADKSCD LGLSMPSKLS

IKDNGNKVAL DGAIGLSSTL AEIFLLEYAQ GMPQAAWGNI

HSEQEWASLL KLHNVQFDLM ARTPYIARHN GTPLLQAISN

ALNPNATESK LPDISPDNKI LFIAGHDTNI ANIAGMLNMR

WTLPGQPDNT PPGGALVFER LADKSGKQYV SVSMVYQTLE

QLRSQTPLSL NQPAGSVQLK IPGCNDQTAE GYCPLSTFTR

VVSQSVEPGC QLQ
```

In some embodiments, the phytase is *Buttiauxella* phytase variant BP-11, having the amino acid sequence set forth in SEQ ID NO: 7, and which includes substitutions at amino acid residues A89, T134, F164, T176, A178, K207, A209, S248, Q256, A261, and N270, relative to the sequence of the wild-type enzyme (SEQ ID NO: 5). The particular substitutions are A89T, T134I, F164S, T176K, A178P, K207E, A209S, S248L, Q256Y, A261E, and N270K.

Mature Protein Sequence of *Buttiauxella* Phytase Variant BP-11 (SEQ ID NO: 7)

```
NDTPASGYQV EKVVILSRHG VRAPTKMTQT MRDVTPNTWP

EWPVKLGYIT PRGEHLISLM GGFYRQKFQQ QGILSQGSCP

TPNSIYVWTD VDQRTLKTGE AFLAGLAPQC GLTIHHQQNL

EKADPLFHPV KAGICSMDKT QVQQAVEKEA QTPIDNLNQH

YIPSLALMNT TLNFSKSPWC QKHSADKSCD LGLSMPSKLS

IKDNGNEVSL DGAIGLSSTL AEIFLLEYAQ GMPQAAWGNI

HSEQEWALLL KLHNVYFDLM ERTPYIARHK GTPLLQAISN

ALNPNATESK LPDISPDNKI LFIAGHDTNI ANIAGMLNMR

WTLPGQPDNT PPGGALVFER LADKSGKQYV SVSMVYQTLE

QLRSQTPLSL NQPAGSVQLK IPGCNDQTAE GYCPLSTFTR

VVSQSVEPGC QLQ
```

In some embodiments, the phytase has at least about 90%, at least about 91%, at least about 92%, at least about 93%, at least about 94%, at least about 95%, at least about 96%, at least about 97%, at least about 98% and even at least about 99% sequence identity to the amino acid sequence set forth in SEQ ID NO: 5, an alanine at position 92 (as set forth in SEQ ID NO: 6), and at least one of the following amino acids: a threonine at position 89, an isoleucine at position 134, a serine at position 164, a lysine at position 176, a proline at position 178, a glutamic acid at position 207, a serine at position 209, a leucine at position 248, a tyrosine at position 256, a glutamic acid at position 261, and a lysine at position 270.

In some embodiments, the phytase has at least about 90%, at least about 91%, at least about 92%, at least about 93%, at least about 94%, at least about 95%, at least about 96%, at least about 97%, at least about 98% and even at least about 99% sequence identity to the amino acid sequence set forth in SEQ ID NO: 5 and at least one of the following amino acid changes: A89T, D92A, T134I, F164S T176K, A178P, K207E, A209S, S248L, Q256Y, A261E, and N270K.

In some embodiments, the phytase is *Buttiauxella* phytase variant BP-17, having the amino acid sequence set forth in SEQ ID NO: 8, and which includes substitutions at amino acid residues A89, D92, T134, F164, T176, A178, K207, A209, S248, Q256, A261, and N270, relative to the sequence of the wild-type enzyme (SEQ ID NO: 5). The particular substitutions are A89T, D92A, T134I, F164S, T176K, A178P, K207E, A209S, S248L, Q256Y, A261E, and N270K.

Mature Protein Sequence of *Buttiauxella* Phytase Variant BP-17 (SEQ ID NO: 8)

```
NDTPASGYQV EKVVILSRHG VRAPTKMTQT MRDVTPNTWP

EWPVKLGYIT PRGEHLISLM GGFYRQKFQQ QGILSQGSCP

TPNSIYVWTD VAQRTLKTGE AFLAGLAPQC GLTIHHQQNL

EKADPLFHPV KAGICSMDKT QVQQAVEKEA QTPIDNLNQH

YIPSLALMNT TLNFSKSPWC QKHSADKSCD LGLSMPSKLS

IKDNGNEVSL DGAIGLSSTL AEIFLLEYAQ GMPQAAWGNI

HSEQEWALLL KLHNVYFDLM ERTPYIARHK GTPLLQAISN

ALNPNATESK LPDISPDNKI LFIAGHDTNI ANIAGMLNMR

WTLPGQPDNT PPGGALVFER LADKSGKQYV SVSMVYQTLE

QLRSQTPLSL NQPAGSVQLK IPGCNDQTAE GYCPLSTFTR

VVSQSVEPGC QLQ
```

In some embodiments, the phytase is a fragment of an amino acid sequence comprising at least about 90%, at least about 91%, at least about 92%, at least about 93%, at least about 94%, at least about 95%, at least about 96%, at least about 97%, at least about 98% and even at least about 99% sequence identity to SEQ ID NO: 5, wherein the fragment comprises at least 350 amino acids, at least 375 amino acid or even at least 400 amino acids. In some embodiments, the fragments display phytase activity. In some embodiments, the fragments display at least about 50%, at least about 60%, at least about 70%, at least about 80%, at least about 90% at least about 95%, and even at least about 99% of the phytase activity of the phytase of SEQ ID NO: 5.

Methods for identification of suitable phytases, including those from *Buttiauxella* spp. are known in the art (see, e.g., WO 06/043178).

C. Secondary Enzymes and Components

The compositions and methods may optionally include other enzymes, including but are not limited to α-amylases, acid fungal proteases, other GA, other phytases, cellulases, hemicellulases, xylanases, proteases, pullulanases, beta amylases, lipases, cutinases, pectinases, β-glucosidases, galactosidases, esterases, cyclodextrin transglycosyltransferases (CGTases), oxido-reductases, esterases, β-amylases, and combinations thereof. In some embodiments, the secondary enzyme is a second GA, including any GA mentioned, above. In some embodiments the additional enzyme is a second phytase, including any bacterial or fungal phytase, such as those mentioned, above.

In some embodiments, the additional enzyme is an α-amylase, such as an acid stable α-amylase which, when added in an effective amount, has activity in the pH range of about 3.0 to about 7.0, including from about 3.5 to about 6.5. α-amylases that find use in the present invention include but are not limited to, fungal α-amylases or bacterial α-amylases. In some embodiments, the α-amylase is a wild-type α-amylase, a variant or fragment thereof, or a hybrid α-amylase that is derived from, for example, a catalytic domain from one enzyme and a starch binding domain from another. α-amylases include acid stable α-amylases and α-amylases having granular starch hydrolyzing activity (GSHE).

In some embodiments, α-amylases include those obtained from filamentous fungal strains including but not limited to strains such as *Aspergillus* (e.g., *A. niger*, *A. kawachi*, and *A. oryzae*); *Trichoderma* spp., *Rhizopus* spp., *Mucor* spp., and *Penicillium* spp. In some embodiments, the α-amylase is obtained from a strain of *Aspergillus kawachi* or a strain of *Trichoderma reesei*. In some embodiments, the α-amylase is a GSHE such as TrAA or AkAA. In some embodiments, the α-amylase is a hybrid enzyme comprising a fragments derived from enzymes obtained from *A. kawachi* and *A. niger*.

Additional α-amylases useful as secondary enzymes include those obtained from bacteria such as *Bacillus* (e.g., *B. licheniformis*, *B. lentus*, *B. coagulans*, *B. amyloliquefaciens*, *B. stearothermophilus*, *B subtilis*, and hybrids, mutants and variants thereof (see, e.g., U.S. Pat. Nos. 5,763,385, 5,824, 532, 5,958,739, 6,008,026, and 6,361,809). Some of these amylases are commercially available, e.g., TERMAMYL®, LIQUEZYME® SC, and SUPRA® available from Novo Nordisk A/S, ULTRATHIN® from Diversa, and SPEZYME® FRED, SPEZYME® XTRA, and GZYME® G997 available from Danisco US, Inc, Genencor Division.

In some embodiments, the secondary enzyme is a cellulase. Cellulases are enzymes that hydrolyze cellulose (β-1,4-D-glucan linkages) and/or derivatives thereof, such as phosphoric acid swollen cellulose. Cellulases include exo-cellobiohydrolases (CBH), endoglucanases (EG) and β-glucosidases (BG) (EC3.2.191, EC3.2.1.4 and EC3.2.1.21). Examples of suitable cellulases include, but are not limited to, those from *Penicillium*, *Trichoderma*, *Humicola*, *Fusarium*, *Thermomonospora*, *Cellulomonas*, *Clostridium*, and *Aspergillus*. Commercially available cellulases sold for feed applications include β-glucanases such as ROVABIO® (Adisseo), NATUGRAIN® (BASF), MULTIFECT® BGL (Danisco Genencor), and ECONASE® (AB Enzymes).

In some embodiments, the secondary enzyme is a xylanase. Xylanases (e.g. endo-β-xylanases (E.C. 3.2.1.8)) hydrolyze xylan backbone chains. Suitable xylanases include those obtained from bacterial sources (e.g., *Bacillus*, *Streptomyces*, *Clostridium*, *Acidothermus*, *Microtetrapsora*, and *Thermonospora*), and from fungal sources (e.g., *Aspergillus*, *Trichoderma*, *Neurospora*, *Humicola*, *Penicillium*, and *Fusarium* (see, e.g., EP 473 545, U.S. Pat. No. 5,612,055, WO 92/06209, and WO 97/20920). Commercial preparations include MULTIFECT® and FEEDTREAT® Y5 (Danisco US, Inc. Genencor Division), RONOZYME® WX (Novozymes A/S), and NATUGRAIN® WHEAT (BASF).

In some embodiments, the secondary enzyme is a protease. In some embodiments, the protease is obtained from *Bacillus* (e.g., *B. amyloliquefaciens*, *B. lentus*, *B. licheniformis*, and *B. subtilis*). These enzymes include subtilisins (see, e.g., U.S. Pat. No. 4,760,025). Suitable commercial protease include MULTIFECT® P 3000 (Danisco US, Inc. Genencor Division) and SUMIZYME® FP (Shin Nihon). In some embodiments, the protease is derived from a fungal source (e.g., *Trichoderma* NSP-24, *Aspergillus*, *Humicola*, and *Penicillium*). In some embodiments, the protease is an acid fungal protease (AFP) including but not limited to those obtained from *Aspergillus*, *Trichoderma*, *Mucor* and *Rhizopus*, such as *A. niger*, *A. awamori*, *A. oryzae*, and *M. miehei*. Proteases can be obtained from the heterologous or endogenous protein expression of bacteria, plants, and fungi sources. Proteases include naturally occurring wild-type proteases as well as variant and genetically engineered mutant proteases, including those described in U.S. Pat. No. 7,429,476.

In some embodiments, the secondary component is at least one fermenting organism.

IV. Compositions

One aspect of the present compositions and methods is a composition comprising blended or formulated enzymes, including at least one glucoamylase and at least one phytase. In some embodiments, the phytase is a *Buttiauxella* spp. phytase. In particular embodiments, the phytase is a BP-WT, BP-11, or BP-17 phytase. In some embodiments, the phytase has at least about 90% sequence identity to SEQ ID NO: 5.

In some embodiments, the phytase has at least about 85%, at least about 90%, at least about 91%, at least about 92%, at least about 93%, at least about 94%, at least about 95%, at least about 96%, at least about 97%, at least about 98%, or even at least about 99% sequence identity to SEQ ID NO: 5 and, optionally, an alanine at position 92. The phytase may further include other mutations described herein.

In some embodiments, the enzyme components of the composition are a blended formulation comprising at least the two enzyme components mixed together. In some embodiments, the compositions comprise a GA and phytase formulated in a suitable enzyme formulation. In some embodiments, the formulated enzyme composition provides a specific preselected ratio of GA and phytase and, optionally, other secondary enzymes. In some embodiments, the enzyme components are individually added during one or more process steps to produce a composition comprising the two enzymes. This may involve adding the separate components of the composition in a time or step-wise manner such that a ratio is maintained, or adding the components simultaneously.

In some embodiments, the amount of phytase used is from about 0.01 to about 10 FTU/g, including about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.25, 0.28, 0.3, 0.35, 0.4, 0.45, 0.5, 0.55, 0.6, 0.65, 0.7, 0.75, 0.8, 0.85, 0.9, 0.95, 1.0, 1.1, 1.5, 1.8, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, and 20. Larger amounts of phytase can also be used. In some embodiments, the about of phytase used is from about 0.01 to about 1.0 FTU/g. In some embodiments, the amount of phytase used is at least about 0.01 FTU/g, including at least about 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.25, 0.28, 0.3, 0.35, 0.4, 0.45, 0.5, 0.55, 0.6, 0.65, 0.7, 0.75, 0.8 FTU/g.

V. Methods of Use

Another aspect of the present compositions and methods relates to a method for using a glucoamylase in combination with a phytase during saccharification, fermentation, and/or SSF in starch a conversion processes, resulting in a process that produces less phytic acid end-products and/or by-products than are produced using conventional methods. In some embodiments, the method includes at least one liquefaction step prior to saccharification, fermentation, and/or SSF. In some embodiments, the process results in DDGS with reduced phytic acid compared to conventional methods. In some embodiments, the process results in ethanol and provides thin stillage with reduced phytic acid compared to conventional methods.

Various types of plant material can be used with the present methods. In some embodiments, the plant material is grain. In some embodiments, the plant material is obtained from wheat, corn, rye, sorghum (e.g., milo), rice, millet, barley, triticale, cassava (e.g., tapioca), potato, sweet potato, sugar beets, sugarcane, and legumes such as soybean and peas, and combinations thereof. Plant materials include hybrid varieties and genetically modified varieties (e.g., transgenic corn, barley, or soybeans comprising heterologous genes). Any part of the plant can be used as a substrate, including but not limited to, leaves, stems, hulls, husks, tubers, cobs, grains, and the like. In some embodiments, essentially the entire plant is used, for example, the entire corn stover. In some embodiments, whole grain is used as a source of granular starch. Whole grains include corn, wheat, rye, barley, sorghum, and combinations thereof. In other embodiments, granular starch is obtained from fractionated cereal grains including fiber, endosperm, and/or germ components. Methods for fractionating plant material, such as corn and wheat, are known in the art. In some embodiments, plant material obtained from different sources is mixed (e.g. corn and milo or corn and barley).

In some embodiments, the plant material is prepared by means such as milling. Two general milling processes are wet milling and dry milling. In dry milling, the whole grain is milled and used, while in wet milling, the grain is separated (e.g., the germ from the meal). Means of milling whole cereal grains are known and include the use of hammer mills and roller mills. Reference is made to THE ALCOHOL TEXTBOOK: A REFERENCE FOR THE BEVERAGE, FUEL AND INDUSTRIAL ALCOHOL INDUSTRIES 3 ED. K. A. Jacques et al., Eds, (1999) Nottingham University Press. See, Chapters 2 and 4.

In some embodiments, the plant material containing a starch substrate is hydrolyzed and/or liquefied using an α-amylase to produce oligosaccharides. In some embodiments, an alpha α-amylase is added to a slurry of milled starch substrate (e.g., milled grain) to produce a liquefact containing dextrins and/or oligosaccharides. The skilled person will be able to determine the effective dosage, pH, and contact time of α-amylase to be used in the processes. The optimal usage level in a liquefaction depends upon processing parameters such as type of plant material, viscosity, processing time, pH, temperature and ds.

VI. Sequential and Simultaneous Saccharification and Fermentation

The liquefact containing dextrins and/or oligosaccharides from the liquefaction may subsequently be subjected to saccharification, fermentation, and/or simultaneous saccharification and fermentation (SSF). Saccharification further reduces the sugars in a liquefact containing dextrins, and/or oligosaccharides to fermentable sugars. The fermentable sugars are then converted by fermenting microorganisms to obtain end-products such as alcohols and DDGS, which can be recovered using a suitable method.

In some embodiments, saccharification and fermentation occur simultaneously, in a process called simultaneous saccharification fermentation (SSF). In some embodiments the saccharification and fermentation occur separately. In some embodiments, the GA/phytase enzyme composition is added during a pre-saccharification step, during the saccharification process, during the fermentation process, or during the SSF process.

In some embodiments, the saccharification process lasts for 12 to 120 hours. However, it is common to perform a pre-saccharification step for 30 minutes to 2 hours (including for example, 30 to 60 minutes) and then to complete saccharification during fermentation. Saccharification is commonly carried out at temperatures of 30 to 65° C. and typically at pH of 4.0 to 5.0. Where a pre-saccharification step is included, the phytase is added during the pre-saccharification step.

Any of the GA described herein find use as saccharfying enzymes. In some embodiments, the enzyme compositions are added at the beginning of the saccharification step as a GA/phytase blend. In other embodiments, the GA and phytase are added separately. In some embodiments, the GA is added at the beginning of the saccharification step and the phytase is added later but before the fermentation step is completed. In some embodiments, saccharification and fermentation are conducted simultaneously and a GA/phytase blend is added during simultaneous saccharification/fermentation (SSF).

In some embodiments the resulting fermentable sugars are subjected to fermentation with fermenting microorganisms. In some embodiments, the contacting step and the fermenting step are performed simultaneously in the same reaction vessel. In other embodiments, these steps are performed sequentially. Fermentation processes are generally described in *The Alcohol Textbook* 3$^{rd}$ ED, *A Reference for the Beverage, Fuel and Industrial Alcohol Industries*, Eds. Jacques et al., (1999) Nottingham University Press, UK.

The fermentable sugars or dextrins (e.g. glucose) resulting from the saccharification may be used as a fermentation feedstock in microbial fermentations under suitable conditions to obtain end-products, such as alcohol (e.g., ethanol), organic acids (e.g., succinic acid, lactic acid), sugar alcohols (e.g., glycerol), ascorbic acid intermediates (e.g., gluconate, DKG, KLG) amino acids (e.g., lysine), and/or proteins (e.g., antibodies and fragment thereof).

The fermentable sugars may be fermented with yeast at temperatures in the range of about 15 to about 40° C., about 20 to about 38° C., and even about 25 to about 35° C.; at a pH range of about 3.0 to about 6.5; about 3.0 to about 6.0; about 3.0 to about 5.5, about 3.5 to about 5.0, and even about 3.5 to about 4.5; and for a period of time of about 5 hrs to about 120 hours, including about 12 to about 120 and from about 24 to about 90 hours, to produce an alcohol product, such as ethanol.

Yeast cells may be provided in an amount of about $10^4$ to about $10^{12}$ cells, or from about $10^7$ to about $10^{10}$ viable yeast cells per ml of fermentation broth. The fermentation process may include the addition of raw materials, such as nutrients, acids, and additional enzymes, as well as supplements such as vitamins (e.g., biotin, folic acid, nicotinic acid, riboflavin), cofactors, macro-nutrients, micro-nutrients and salts (e.g., $(NH4)_2SO_4$; $K_2HPO_4$; NaCl; $MgSO_4$; $H_3BO_3$; $ZnCl_2$; and $CaCl_2$).

VII. Fermenting Organisms

Any suitable fermenting organism may be used with the present compositions and methods. Examples of suitable fermenting organisms are ethanologenic microorganisms or ethanol producing microorganisms such as ethanologenic bacteria which express alcohol dehydrogenase and pyruvate dehydrogenase, which can be obtained from *Zymomonas moblis* (see e.g., U.S. Pat. Nos. 5,000,000, 5,028,539, 5,424,202, 5,514,583, and 5,554,520). The ethanologenic microorganisms may express xylose reductase and xylitol dehydrogenase, which are enzymes that convert xylose to xylulose. Alternatively or additionally, xylose isomerase is used to convert xylose to xylulose. A microorganism capable of fermenting both pentoses and hexoses to ethanol may be utilized. The microorganism can be a naturally-occurring or non-genetically engineered microorganism or an engineered or recombinant microorganism.

Fermenting microorganisms include bacterial strains from *Bacillus, Lactobacillus, E. coli, Erwinia, Pantoea* (e.g., *P. citrea*), *Pseudomonas* and *Klebsiella* (e.g., *K. oxytoca*) (see e.g., U.S. Pat. Nos. 5,028,539 and 5,424,202 and WO 95/13362). The fermenting microorganism selected depends on the end-product to be produced.

The ethanol-producing microorganism may be a fungal microorganism, such as a *Saccharomyces* strain including but not limited to *S. cerevisiae* (see, e.g., U.S. Pat. No. 4,316,956). A variety of *S. cerevisiae* are commercially available and include but are not limited to FALI® (Fleischmann's Yeast), SUPERSTART® (Alltech), FERMIOL® (DSM Specialties), RED STAR® (Lesaffre), and ANGEL ALCOHOL YEAST® (Angel Yeast Company, China).

VIII. Recovery of Alcohol, DDGS and Other End-Products

End-products of a fermentation process may be an alcohol (e.g., ethanol or butanol), which can be separated and/or purified from the fermentation media. Methods for separation and purification are known in the art and include methods such as subjecting the media to extraction, distillation, column chromatography, molecular sieve dehydration, or ultra filtration. The end-product may be identified directly by submitting the media to high-pressure liquid chromatography (HPLC) or gas chromatography (CG) analysis.

Where the end-product is ethanol, it may be used for fuel, cleaning, or chemical synthesis, or injected as a beverage. Fermentation co-products such as distillers dried grains (DDG) and distiller's dried grain plus solubles (DDGS) can be used as an animal feed.

The present compositions and methods can reduce the phytic acid content of the fermentation broth, the thin stillage and/or the co-products of the fermentation such as distillers dried grains (DDG); distillers dried grains with solubles (DDGS); distillers wet grains (DWG), and distillers wet grains with solubles (DWGS). For example, the compositions and methods can reduce the phytic acid content of fermentation filtrate by at least about 60%, at least about 65%, at least about 70%, at least about 75%, at least about 80%, at least about 85% and even at least about 90% or more as compared to essentially the same process but without the phytase. The amount of phytate found in the DDGS can be reduced by at least about 50%, at least about 70%, at least about 80% and at least about 90% as compared to the phytate content in DDGS from a corresponding process which is essentially the same as the claimed process but without a phytase pretreatment incubation. For example, while the % phytate content in commercial samples of DDGS may vary, a general range of % phytate is be from about 1% to about 3% or higher. In comparison, the % phytate in the DDGS obtained using the current process is less than about 1.0%, less than about 0.8% and even less than about 0.5%. DDGS can be added to an animal feed before or after pelletization and may include active phytase In some industrial ethanol processes, ethanol is distilled from the filtrate resulting in a thin stillage portion that is suitable for recycling into the fermentation stream. Using the present compositions and methods, the thin stillage has a lower phytic acid content compared to that obtained using a conventional method. The reduction in phytic acid may result from the addition of phytase during a pretreatment step, during saccharification, during saccharification/fermentation, or a combination, thereof. The reduction in phytic acid content of the thin stillage may be at least about 60%, at least about 65%, at least about 70%, at least about 75%, at least about 80%, at least about 85% or even at least about 90% or more, compared to essentially the same process but without the phytase. Similarly, the amount of phytate found in the thin stillage can be reduced by at least about 50%, at least about 60%, at least about 70%, at least about 80% or even at least about 90% compared to the phytate content in thin stillage resulting from an otherwise similar process that lacks a phytase.

Other aspects and embodiments of the compositions and methods will be apparent to the skilled person in view of the disclosure.

EXAMPLES

The following examples are offered to illustrate, but not to limit the compositions and methods.

In the disclosure and experimental section that follows, the following abbreviations apply: wt % (weight percent); ° C. (degrees Centigrade); $H_2O$ (water); $dH_2O$ (deionized water); $dIH_2O$ (deionized water, Milli-Q filtration); g or gm (grams); μg (micrograms); mg (milligrams); kg (kilograms); μL (microliters); ml and mL (milliliters); mm (millimeters); μm (micrometer); M (molar); mM (millimolar); μM (micromolar); U (units); MW (molecular weight); sec (seconds); min(s) (minute/minutes); hr(s) (hour/hours); ds (dry solids); DO (dissolved oxygen); W/V (weight to volume); W/W (weight to weight); V/V (volume to volume); Genencor (Danisco US, Inc., Genencor Division, Palo Alto, Calif.); IKA (IKA Works Inc. 2635 North Chase Parkway SE, Wilmington, N.C.); MT (Metric ton); Ncm (Newton centimeter); GAU (glucoamylase activity unit; FTU (phytase activity unit) and ETOH (ethanol).

Example 1

Viscosity Measurements

A glass cooker—viscometer, LR-2.5T system IKA was used to determine viscosity. In brief, the viscometer consists of a 2,000 ml double-walled glass vessel with an anchor mixer that is stirred by a Eurostar Labortechnik power control-viscometer. The viscosity range of the viscometer is 0-600 Ncm.

In general, a slurry comprising a starch substrate and an appropriate amount of enzyme was poured into the viscometer vessel. The temperature and viscosity were recorded during heating to 85° C. and incubation was continued for additional 60 to 120 mins. Viscosity was measured in Ncm and recorded at intervals.

Example 2

Use of a Glucoamylase and a Phytase in Ethanol Fermentation

This example shows the efficacy of glucoamylase (GA) and phytase in ethanol fermentation for producing DDGS and thin stillage with a lower phytate content than obtained using a conventional method. The GA used was the *Trichoderma reesei* GA (TrGA) corresponding to SEQ ID NO: 1 (see e.g., U.S. Pat. Nos. 7,354,752 and 7,413,887). The phytase used was *Buttiauxella* phytase, BP-17 corresponding to SEQ ID NO: 8.

Glucoamylase activity units (GAU) were defined as the amount of enzyme required to produce 1 g of reducing sugar calculated as glucose per hour from a soluble starch substrate at pH 4.2 and 60° C. The PNPG assay is used to measure the activity of glucoamylase.

Phytase activity (FTU) was measured by the release of inorganic phosphate, which forms a yellow complex with acidic molybdate/vandate reagent that can be measured at a wavelength of 415 nm in a spectrophotometer. The released inorganic phosphate was quantified with a phosphate standard curve. One unit of phytase (FTU) was defined as the amount of enzyme that releases 1 micromole of inorganic phosphate from phytate per minute under the reaction conditions given in the European Standard (CEN/TC 327, 2005-TC327WI003270XX).

To measure phytic acid content, phytic acid was extracted from a sample by adjusting the pH of a 5% slurry (for dry samples) to pH 10.0, and then using an HPLC ion exchange column to bind the phytic acid, which was eluted from the column using a NaOH gradient system. The phytic acid content in the liquid was calculated by comparing phytic acid to a standard.

Example 3

Use of TrGA and BP17 in Yeast Fermentation—Effect on DDGS

DDGS (Distillers Dry Grain Solids with Solubles), a component in some animal feeds that is derived from ethanol processing plants, contains phytic acid that is non-digestible by non-ruminants like poultry, fish and pigs. The phytic acid then is discharged through manure resulting in a phosphate pollution. As shown in this example, adding a phytic acid hydrolyzing enzyme like phytase in combination with glucoamylase during the simultaneous saccharification/fermentation process reduces the levels of phytic acid in DDGS.

A liquefact from a conventional starch liquefaction process using corn as the feedstock was prepared and frozen for use in the experiment. The liquefact was thawed, 200 ppm urea was added, and the solids were adjusted to 32.9% ds prior to adjusting the pH to 4.2 with 6N sulfuric acid. Fermentations were conducted in 250 ml flasks containing an aliquot of 200 gm of mash (i.e., the liquefact-containing mixture). The enzymes were diluted so that 1.0 ml of each at the designated activity was added to the flasks. Each condition was replicated. The flasks were inoculated by adding 1 ml of 10% yeast slurry containing 1% glucose about one hour prior to use. BP-17 phytase was added in the 1.0 ml sample at different levels of activity (0, 0.1, 0.25, 0.5, 1.0, 3.0, and 5.0 FTU/gds corn) during simultaneous saccharification/fermentation. *Trichoderma* GA was also added to hydrolyze the soluble dextrins for providing glucose. After the fermentation, the DDGS was analyzed for free phosphorous/free phosphate. Free phosphate was determined by following the colorimetric method of Fiske-Subbarow (see e.g., Fiske, C. H. and Subbarow, Y. (1925) *J. Biol. Chem.* 66:375-400). The samples were ground in a Tekmar analytical mill and free phosphate was extracted in water by adding 1 g of sample to a 100 ml volumetric flask containing 80 ml water. A magnetic bar was added to each flask and they were stirred for 1 hour at room temperature. The flasks were then brought to volume with water, mixed well, and filtered through Whatman no. 1 filter paper. The flasks were placed in a 32° C. water bath, and occasionally mixed. The filtrates were then assayed for phosphate as follows. To 3.0 ml of sample, 1 ml of acid molybdate reagent was added, followed by 1 ml of reducing reagent, and the absorbance of the color developed at room temperature for 20 minutes was measured at 660 nm. The phosphate level in the samples was then calculated from a phosphate standard curve. The final results were calculated as µg phosphorus per g of sample.

FIG. 1 is a graph showing the effect of BP-17 phytase concentration during yeast fermentation on the phytic acid reductions. In these experiments, 32% whole ground corn containing 50% thin stillage was used at a pH of 4.2 containing 0.325 GAU/gds, GC147. The graph shows that the level of free phosphorous reached a plateau of about 0.75% free phosphorous with the addition of about 0.7 FTU/g phytase. Thus, the levels of phytic acid were reduced with the addition of a very small amount of phytase, i.e., 0.1 FTU/gds, such that more than 80% of the phytic acid was removed.

All publications and patents mentioned herein are expressly incorporated by reference. Various modifications and variations will be apparent to those skilled in the art without departing from the scope and spirit of the invention.

What is claimed is:

1. A method of producing an alcohol, comprising:
   (a) contacting a slurry comprising a starch substrate with at least one α-amylase, thus producing oligosaccharides;
   (b) contacting the oligosaccharides with at least one glucoamylase and at least one phytase, wherein the phytase has at least 98% amino acid sequence identity to SEQ ID NO: 5 and comprises substitutions at positions corresponding to positions 89, 92, 134, 164, 207, 209, 248, 256 and 261 of SEQ ID NO: 5, and wherein % identity is determined by the CLUSTAL-W program in MacVector version 6.5, operated with default parameters, including an open gap penalty of 10.0, an extended gap penalty of 0.1, and a BLOSUM 30 similarity matrix, to produce fermentable sugars; and
   (c) fermenting the fermentable sugars in the presence of a fermenting organism to produce alcohol.

2. The method of claim 1, wherein steps (b) and (c) occur simultaneously.

3. The method of claim 1, further comprising raising the temperature above the gelatinization temperature of the starch substrate after step (a) and before step (b).

4. The method of claim 1, wherein the starch substrate is a milled grain and the milled grain is selected from the group consisting of maize, barley, wheat, rice, sorghum, rye, millet, and triticale.

5. The method of claim 1, wherein the substitutions are substitutions corresponding to substitutions A89T, D92A, T134I, F164S, K207E, A209S, S248L, Q256Y and A261E in SEQ ID NO: 5.

6. The method of claim 1, further comprising contacting the oligosaccharides with at least one other enzyme selected from the group consisting of a second α-amylase, a second glucoamylase, a second phytase, a cellulase, a pullulanase, a protease, and a laccase.

7. The method of claim 1, wherein the alcohol is ethanol.

8. The method of claim 1, further comprising recovering the alcohol.

9. The method of claim 1, further comprising recovering distillers dried grains with solubles (DDGS).

10. A method of reducing phytic acid during ethanol fermentation, comprising:
    (a) contacting a slurry comprising a starch substrate with at least one α-amylase;
    (b) contacting the starch substrate with at least one glucoamylase and at least one phytase, wherein the phytase has at least 98% amino acid sequence identity to SEQ ID NO: 5 and comprises substitutions at positions corresponding to positions 89, 92, 134, 164, 207, 209, 248, 256 and 261 of SEQ ID NO: 5, wherein % identity is determined by the CLUSTAL-W program in MacVector version 6.5, operated with default parameters, including an open gap penalty of 10.0, an extended gap penalty of 0.1, and a BLOSUM 30 similarity matrix, and wherein the phytase catalyzes the hydrolysis of phytic acid in the starch substrate to reduce phytic acid, under conditions such that fermentable sugars are produced; and
    (c) fermenting the fermentable sugars in the presence of a fermenting organism under conditions that produce ethanol and/or distillers dried grains with solubles (DDGS).

11. The method of claim 10, further comprising a step of raising the temperature above the liquefaction temperature of the starch substrate.

12. The method of claim 10, wherein steps (b) and (c) occur simultaneously.

13. The method of claim 10, further comprising recovering the ethanol and/or DDGS.

14. The method of claim 10, wherein the glucoamylase is from a filamentous fungus selected from the group consisting of Trichoderma, Penicillium, *Taleromyces, Aspergillus*, and Humicola.

15. The method of claim 14, wherein the *Trichoderma* is *Trichoderma reesei*.

16. The method of claim 10, wherein the DDGS comprises active phytase.

17. The method of claim 10, wherein the starch substrate is a milled grain.

18. The method of claim 17, wherein the grain is selected from the group consisting of maize, barley, millet, wheat, rice, sorghum, rye, and triticale.

19. A method of reducing phytic acid in distillers dried grains with solubles (DDGS), comprising:
    (a) contacting a slurry comprising a starch substrate with at least one α-amylase;
    (b) contacting the starch substrate with at least one *Trichoderma reesei* glucoamylase (TrGA) and at least one phytase, wherein the phytase catalyzes the hydrolysis of phytic acid in the starch substrate to reduce phytic acid and wherein the phytase has at least 98% amino acid sequence identity to SEQ ID NO: 5 and comprises substitutions at positions corresponding to positions 89, 92, 134, 164, 207, 209, 248, 256 and 261 of SEQ ID NO: 5, and wherein % identity is determined by the CLUSTAL-W program in MacVector version 6.5, operated with default parameters, including an open gap penalty of 10.0, an extended gap penalty of 0.1, and a BLOSUM 30 similarity matrix, under conditions such that fermentable sugars are produced; and
    (c) fermenting the fermentable sugars in the presence of a fermenting organism to produce ethanol and/or DDGS.

20. The method of claim 19, wherein steps (b) and (c) occur simultaneously.

* * * * *